(12) United States Patent  
Ferrigolo et al.

(10) Patent No.: US 8,628,486 B2  
(45) Date of Patent: Jan. 14, 2014

(54) JOINT FOR AN ORTHOPEDIC BRACE EQUIPPED WITH A RAPID LOCKING AND UNLOCKING SYSTEM

(75) Inventors: Moreno Ferrigolo, Dossobuono (IT); Alberto Turrini, Castel d'Azzano (IT)

(73) Assignee: F.G.P. S.R.L., Dossobuono, Verona (IT)

( * ) Notice: Subject to any disclaimer, the term of this patent is extended or adjusted under 35 U.S.C. 154(b) by 14 days.

(21) Appl. No.: 13/477,480

(22) Filed: May 22, 2012

(65) Prior Publication Data

US 2012/0310358 A1 Dec. 6, 2012

(30) Foreign Application Priority Data

May 30, 2011 (IT) .............................. VR2011A0122

(51) Int. Cl.  
*A61F 5/00* (2006.01)
(52) U.S. Cl.  
USPC ................................................ 602/5; 602/16
(58) Field of Classification Search  
CPC ............................. A61F 5/0123; A61F 5/0585  
USPC ....................................................... 602/5, 16  
See application file for complete search history.

(56) References Cited

U.S. PATENT DOCUMENTS

| 5,938,629 | A | 8/1999 | Bloedau |
| 2004/0049140 | A1 | 3/2004 | Doty et al. |

OTHER PUBLICATIONS

Italian Search Report for IT VR20110122, dated Dec. 15, 2011, The Hague.

*Primary Examiner* — Jason-Dennis Stewart  
(74) *Attorney, Agent, or Firm* — Greenberg Traurig, LLP

(57) ABSTRACT

A locking system to be fitted on a joint device (10) is equipped with means of control of the relative range of motion (R.O.M.) between two rods or uprights (11, 12) connected to it; said joint consists of a pair of plates (13, 14) connected to each other by means of rivets (15) and to the rods or uprights (11, 12) protruding from the joint. This locking system comprises at least one locking device consisting of a stop member (16) which is inserted between a rod (11) and the plate (13) connected to a fixed central element of the joint. Said stop member is activated to move from a retracted position to an inserted position in the joint, at right angles in respect of the plane of the plate (13), by means of a cursor element (18) sliding on a slide (19) positioned in the upper part of a bridge element (20), said cursor element comprising a sloping surface (17) which causes the movement of the stop member (16) from a retracted to an inserted position.

9 Claims, 5 Drawing Sheets

JOINT FOR AN ORTHOPEDIC BRACE EQUIPPED WITH A RAPID LOCKING AND UNLOCKING SYSTEM

RELATED APPLICATION

This application claims the benefit of and priority to Italian Patent Application Number VR2011A000122, filed May 30, 2011, the contents of which are incorporated by reference herein in its entirety.

BACKGROUND

1. Field

This invention concerns a rapid locking and unlocking system for the freedom of movement of a joint with adjustable angular range for braces, which can be used as an aid for joints of the human body such as the knee, the ankle, the elbow or similar.

The system according to the invention was designed and constructed in order to overcome the need, as yet unsolved, of being able to insert and remove the lock of a brace joint in a practical way.

This lock element is intended to lock the angular movement of the brace and consequently of the limb to which it is attached, in order to prevent movements that are undesired and dangerous for the reconstruction of the tissues of the limb, as in the case of post-surgery requiring immobility, for example when the patient has to sit down or stand up and must not put weight on a knee operated on for meniscus problems.

By means of the locking system according to the invention, the brace is locked at 0° in flexion, when the limb is in a non-flexed position, so that the patient's weight load does not worsen the operated limb.

This invention can be applied in the orthopedics industry with particular reference to manufacturers of prostheses and braces.

2. Background Art

As is known, following surgery performed on the legs or arms, it is necessary for the patient on one hand to wear auxiliary equipment, braces or similar, that is to say fixed or mobile equipment that can increase, improve or control the impaired functioning of body parts, and on the other to undergo rehabilitation sessions to restore the limb to ideal conditions.

After surgery involving the ligaments or cartilage membranes, the limb is normally kept in a locked position, at first totally locked and then partially, by means of special orthopedic equipment generally known as braces or knee braces, which are designed to assist and support the weakened joint, absorbing the most intense strains and stresses.

The first exercises recommended are for passive flexion-extension and circumduction: these movements are very useful for stimulating the circulation of the limb and putting the muscular structure to work.

In the last few years, to optimize the initial stage of scarring of the ligament transplant, closed kinetic chain exercises have been widely encouraged since in these exercises both the proximal and the distal ends of the limb are locked.

The equipment currently used in rehabilitation flexion-extension exercises allows passive movement of the joint. This equipment makes it possible to place the limb in a substantially horizontal position, while the body remains in a seated or lying position, and to produce flexion of the limb with a progressive increase of the angle as the rehabilitation sessions proceed.

This traditional equipment normally consists of a frame which presents means of support for the leg or arm, that are held in an extended position, and thrust means or adjustable angular flexion means, with a range of from 0° to 90°, 120° or 140°.

This known equipment is normally equipped with angular adjustment means but not with rapid locking means, which are necessary in order to prevent movements that are undesired and dangerous for the post-surgical reconstruction of the tissues of the limb.

Immobility of the limb is required, for example, when the patient has to sit down or stand up and must not put weight on a knee operated on for meniscus problems, or in other similar conditions, and to date there are no solutions that foresee the insertion or removal of these locks in a simple and rapid way in an adjustable angular range brace.

The only possibility currently available for locking the brace is, therefore, to access the mechanics of the joint for adjusting the angular range. This operation is usually carried out by an orthopedic technician. This operation also requires partial dismantling of the joint (the protection) and the use of appropriate tools for replacement of the lock elements. This operation modifies the R.O.M. limit settings set by the orthopedic technician and this change could cause a different adjustment with possible negative consequences for the rehabilitation.

These operations were also designed to be carried out infrequently. The use of the rapid locking and unlocking of the freedom of movement of an adjustable angular range for braces foresees the easy and independent activation of this locking and unlocking system without it being necessary to use tools or to dismantle parts of the joint.

Document US-A-2004/049140 discloses a locking system fitted on a joint device equipped with means for controlling the range of motions between two rods, the joint comprising a pair of plates connected to each other by rivets and a locking device which comprises a stop connected to a fixed central element.

Document US-A-5938629 discloses a hinge structure having a first and second hinge elements having inner and outer ends with the inner ends being pivotally secured together. One of said hinge elements has a series of ratchet teeth associated therewith.

The other hinge element has a keeper element slidably mounted thereon to engage, and to be disengaged, with the ratchet teeth to cause the hinge elements to be locked and unlocked, respectively, to each other. A cam element on the hinge structure is operatively connected to the keeper element to slidably move the keeper element into or out of engagement with the ratchet teeth.

DESCRIPTION OF THE INVENTION

This invention proposes to provide a rapid locking and unlocking system for the freedom of movement of a joint with adjustable angular range for knee braces or other orthopedic braces, that is able to eliminate or at least reduce the drawbacks described above.

The invention also proposed to provide an innovative locking system of the brace that can prevent movements of the brace and consequently of the limb to which it is attached, in order to prevent movements that are undesired and dangerous for the post-surgical reconstruction of the tissues of the limb.

This is achieved by means of a locking system for joints with adjustable angular range of orthopedic braces, whose features are described in the main claim.

The dependent claims describe advantageous forms of embodiment of the invention.

The main advantages of this solution concern first of all the fact that the system for locking the angular range of joints according to the invention, arising from the need to be able to insert and remove a joint lock of a brace in a practical way, allow the practical and immediate locking of the brace and consequently of the limb to which it is attached.

By means of the locking system according to the invention, the brace can be locked at 0° in flexion, when the limb is in a non-flexed position. The weight load of the patient does not therefore burden the operated limb, such as for example when the patient hast to sit down or stand up and must not put weight on a knee operated on for meniscus problems.

According to the invention, this type of lock can also be easily inserted and removed without tools, such as for example spanners or screwdrivers, making its use feasible several times a day.

DESCRIPTION OF THE DRAWINGS

Other features and advantages of the invention will become clear on reading the description given below of one embodiment, provided as a non-binding example, with the help of the accompanying drawings, in which.

DESCRIPTION OF ONE EMBODIMENT OF THE INVENTION

Figure 1:
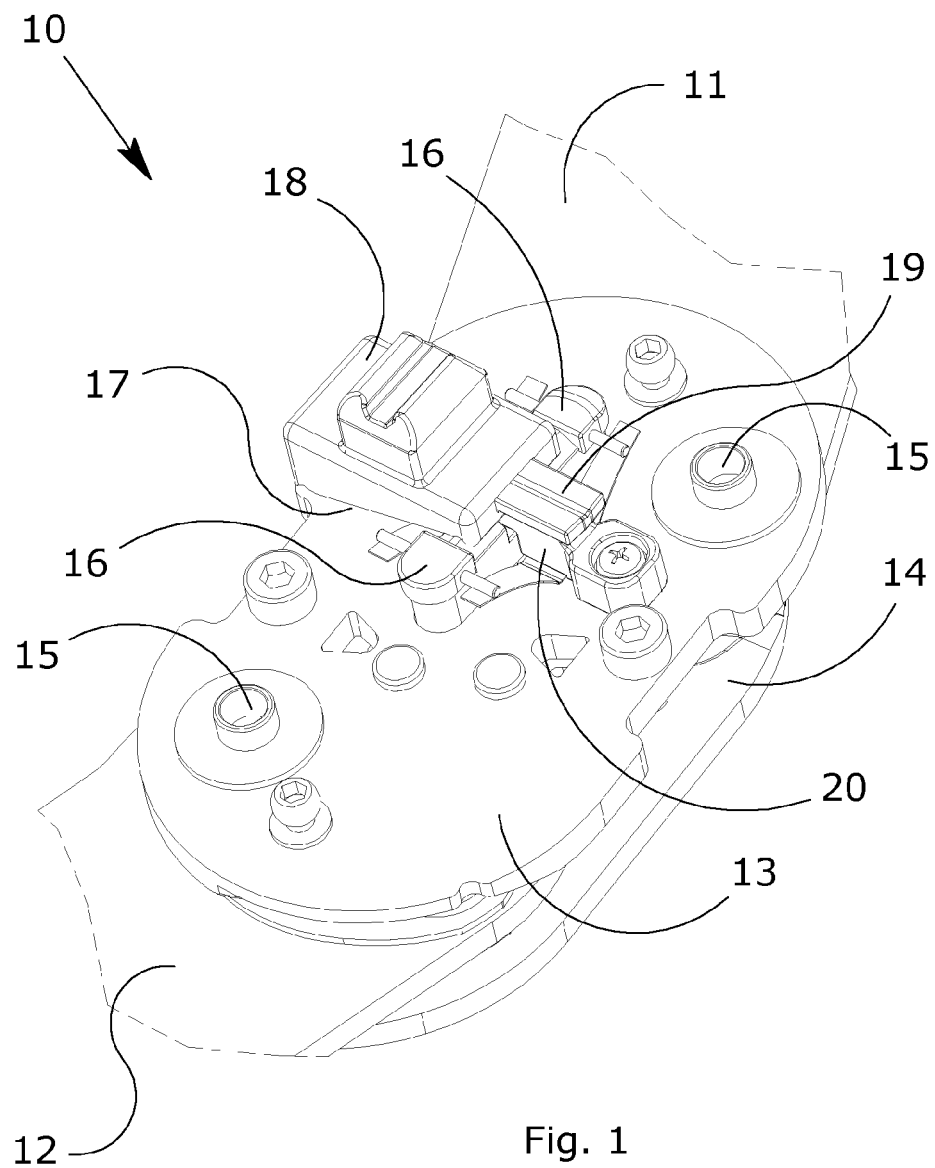
FIG. 1 is a schematic prospective view of the joint provided with locking means according to the invention.

With reference to the accompanying figures, and initially to FIG. 1, the locking system according to the invention can be fitted to a joint device indicated overall with reference number 10 which allows the adjustable angular range between the two uprights 11 and 12, which, in the case of a knee brace, consist respectively of a femoral rod and a tibial rod.

The joint device 10, which is normally equipped with a system for the relative angle of inclination between two rods connected to it (R.O.M.), consists of a pair of plates 13 and 14 connected together by rivets 15 to the bars or uprights 11 and 12 protruding from the joint.

The two rods 11 and 12, which are attached by straps to the leg and made parallel to the femur and the tibia, can move angularly, varying the angle which corresponds to the angle between the femur and the tibia.

The locking system according to the invention is applied as an addition and supplement to the joint without interfering in its function.

Figure 2:
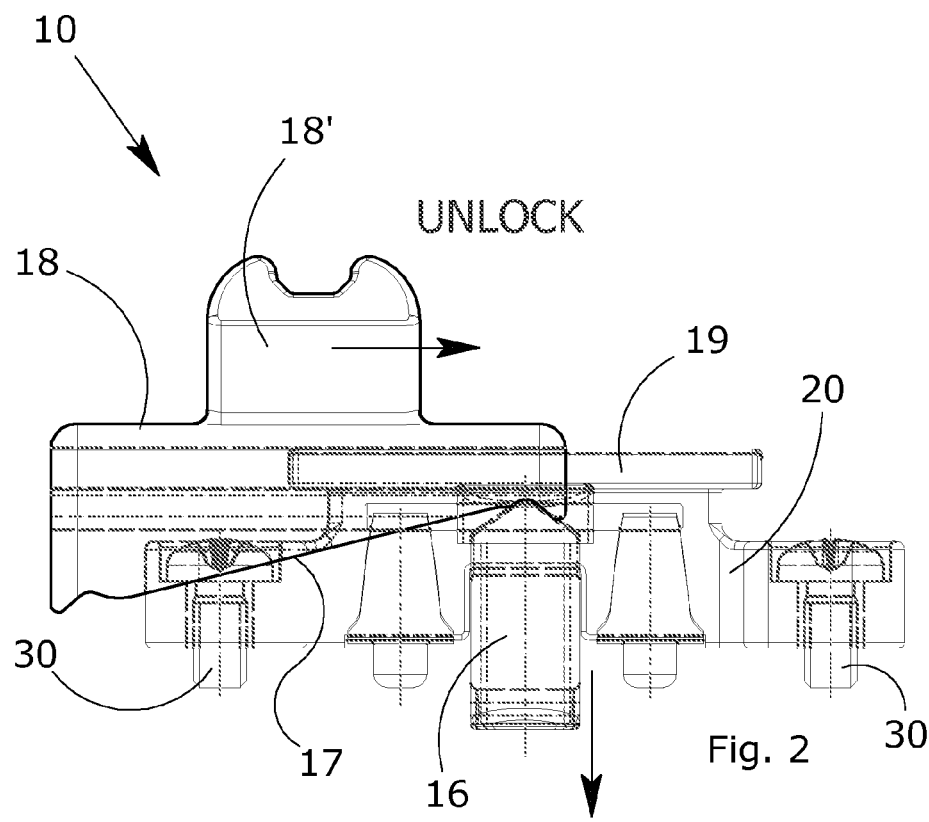
FIGS. 2 and 3 show schematic profile views of the joint in the open unlocked position and in the closed locked position respectively.
Figure 3:
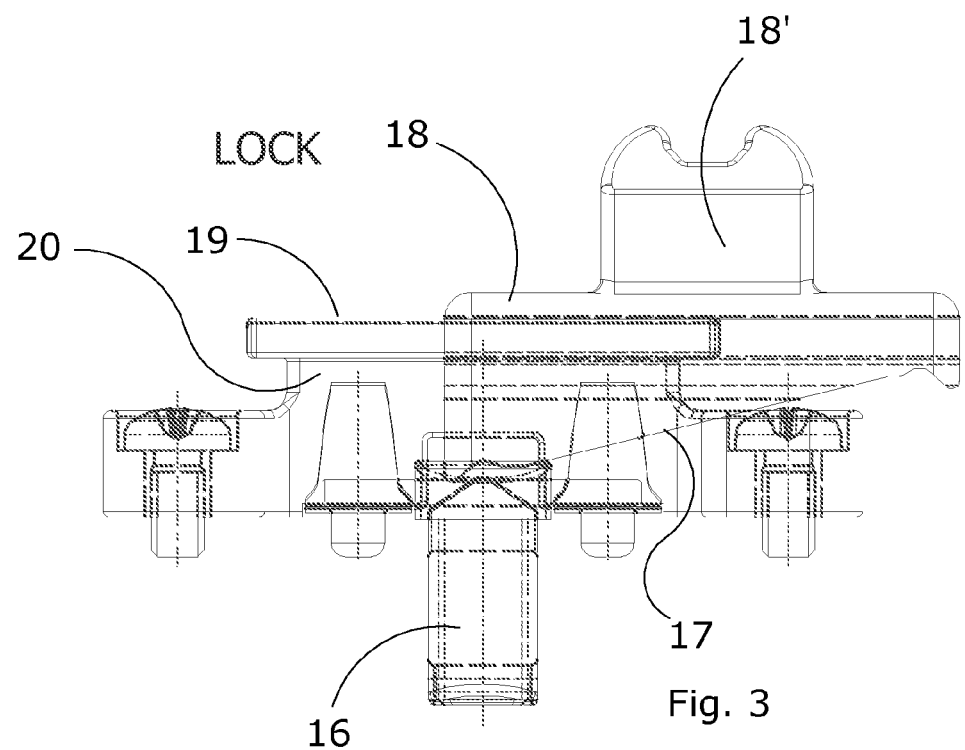

As can be seen in FIGS. 2 and 3, the locking device according to the invention consists of a stop 16 which is inserted between one rod 11 and a fixed central element of the joint, with the dual purpose of acting as an end-of-travel stop for the rods and a support of the stops during flexion and extension. It is fixed rigidly to the plate 13 by means of rivets.

The insertion of the stop 16 prevents the relative movement of the plate 13 and the rod 11 of the joint.

Insertion of the stop 16 is achieved thanks to a sloping surface 17 present on the lower edge of a cursor 18 provided with a thrust tooth 18', wherein the cursor, by sliding in the slide 19 positioned in the upper part of a bridge 20, the latter being fixed on the plate 13, pushes the stop inside the joint, sliding on the crest of the contact surface between the two elements.

The two ends of the sloping surface 17 of the cursor 18 present recesses 21, 22 which make it possible to determine the snap-locking during the movement of the cursor. To move the cursor it is necessary to push it at the two ends to overcome the projections, applying a greater force, making it possible to maintain the cursor in the locking and unlocking positions.

In order to limit the dimensions as much as possible, the travel of the cursor is as large as possible in order to reduce the angle between the sloping surface and the surface of the underlying plate 13.

Figure 5:
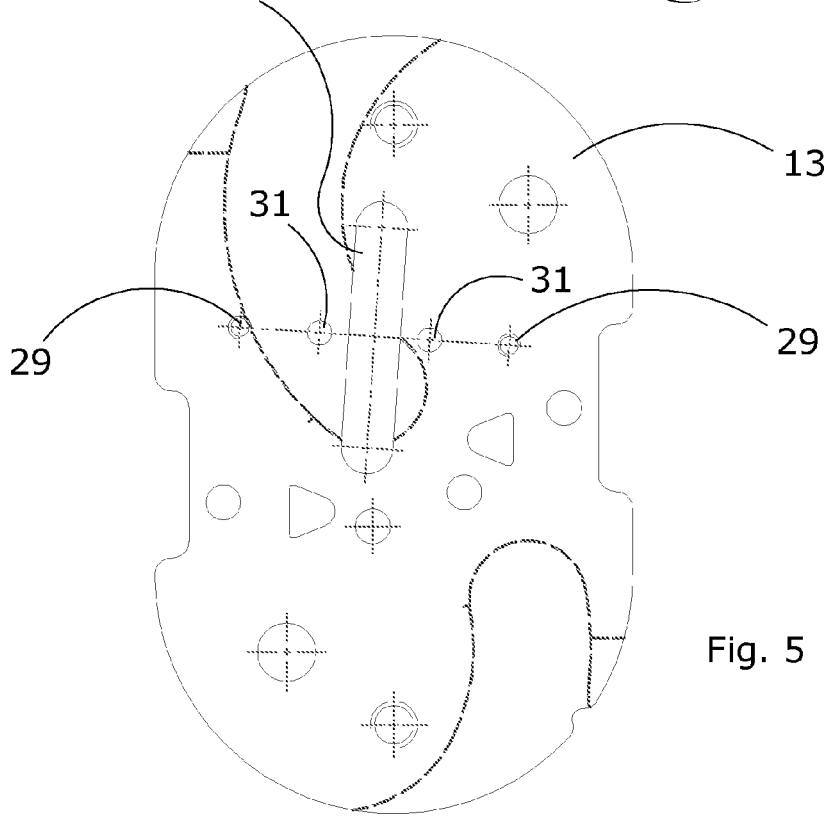
FIG. 5 is a front view of the plate of the adjustable angular range joint, showing the holes to be drilled for insertion of the locking element according to the invention.
Figure 6:
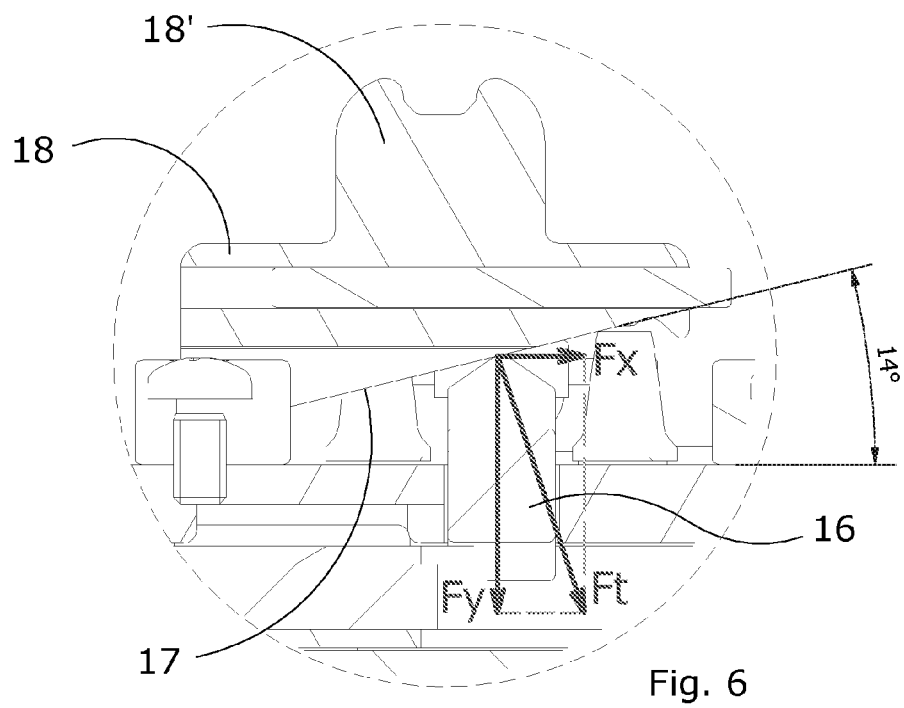
FIG. 6 is a cross-section view along the line A-A of FIG. 7.
Figure 7:
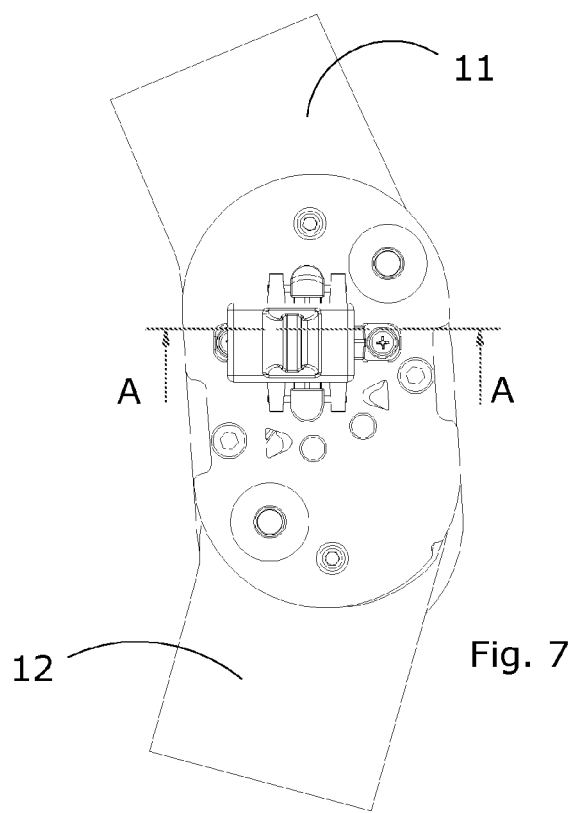
FIG. 7 is a view of the joint with reference to the cross-section line A-A of FIG. 6.

FIG. 6 shows the angle of the sloping surface 17 and how the longitudinal force Fx is distributed in a vectorial way when thrust is applied on the cursor 18. The resulting Ft is distributed along the sloping surface and unloads a vector Fy along the stop, so that the latter is inserted in a slot 23 positioned in the central part of the plate 13, as can be seen in FIG. 5. The stop 16 slides, in fact, in this slot 23 in the plate 13 outside the joint.

To allow the stop 16 to remain in the rest position, that is to say retracted towards the outside of the joint, the system is provided with a pair of springs 24 that act on pins 25 which are stably inserted in the stop 16 parallel to the plate 13. These springs 24 have the dual purpose of causing the stop 16 to return to the retracted position and to create the necessary contrast to the fixing recesses 21 and 22 of the cursor 18.

The upper end of the stop 16 presents an enlarged portion 26 which accommodates the pins 25 and prevents the stop 16 from excessively penetrating the slot 23 in the plate 13. If the stop 16 moves down in an non-parallel way, this enlarged portion makes it possible to stop and return the surface of the plate 13 to a flat position.

Figure 4:
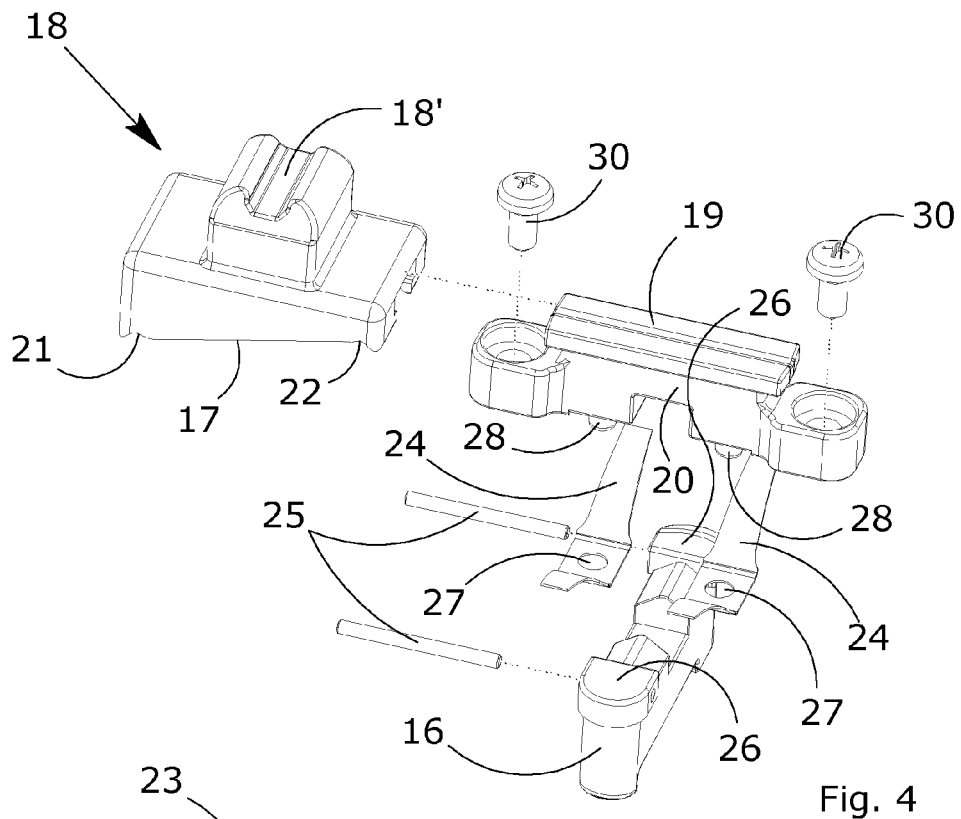
FIG. 4 is an exploded schematic view of the joint according to the invention.

As can be seen in the exploded view in FIG. 4, the springs 24 present holes 27 to accommodate the protruding pins 28 of the bridge 20 and hold them in position. These springs 24 are also held inside two adjacent recesses in the lower part of the bridge 20, creating the housing for the springs 24 to allow their correct dilation.

The system allows the stop 16 to be inserted in the joint and carry out its locking action by applying force on the cursor 18, only when the joint is fully extended, that is to say with flexion=0°.

To prevent the inserted stop 16 from remaining locked by possible compression force applied on it with flexion of the rods, preventing or hindering its unlocking, the unlocking takes place spontaneously thanks to the force of the springs 24. More specifically, when unlocking of the stop 16 is required, the cursor 18 is activated by moving it to the unlocked position (FIG. 2) so that the first time the stop is released from the compression of the rods it will be automatically free to return to the rest position.

This system makes it possible to limit the wear of the stop 16, which would otherwise rub repeatedly on the end of the rods, quickly causing wear of the parts and thus an increase in clearance.

With reference to FIG. 5, to apply this system, it is necessary to drill the following holes in the plate 13:
- a slot 23 to allow the passage of the stop 16;
- two holes 29 for fixing the entire system by means of screws 30;
- two holes 31 to correspond with the pins 28 of the bridge 20 and which fix the springs 24.

Figure 8:
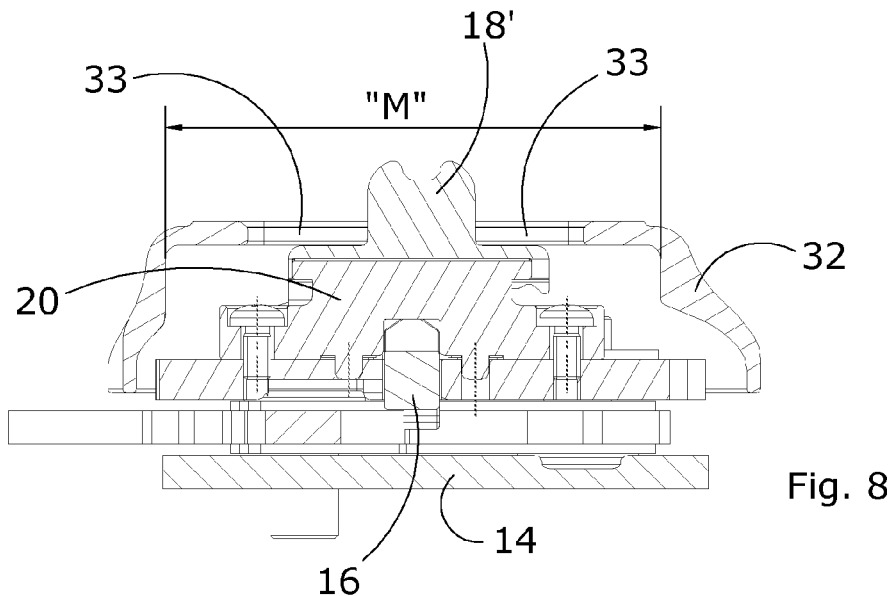
FIG. 8 is a cross-section view along the line B-B of FIG. 9.
Figure 9:
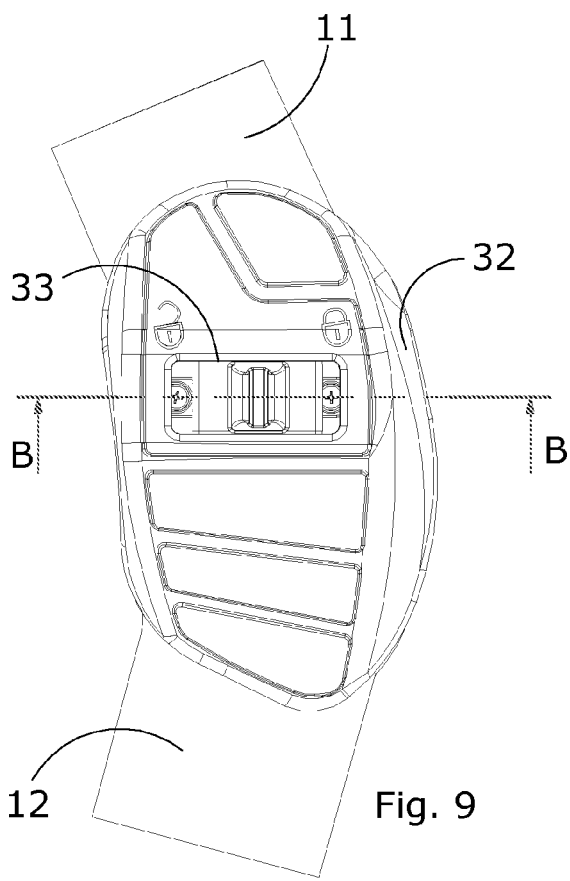
FIG. 9 is a view of the joint with reference to the cross-section line B-B of FIG. 8.
Figure 10:
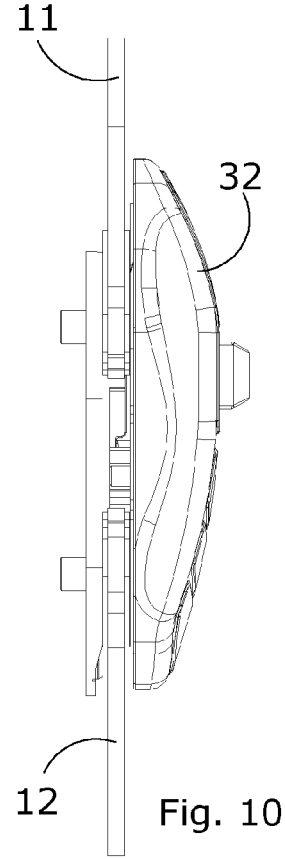
FIG. 10 shows a projected view of FIG. 9 of the joint.

To cover the mechanics of the locking and unlocking system, it is equipped with an appropriate cap 32 (FIGS. 8, 9 and 10) with an opening 33 for the sliding of the thrust tooth of the cursor 18, that is to say the protruding part for the adjustment, and a width which defines the maximum and minimum travel of the cursor. This width, defined with "M", corresponds to the sum of the width of the cursor plus the travel of the cursor 18 plus clearance.

As can be noted, the aims of the invention are achieved by means of the simple but efficient use of the locking and unlocking system described and illustrated, the system foreseeing the insertion of the stop 16 to prevent the relative movement of the plate 13 and the rod 11 of the joint.

The invention is described above with reference to a preferred embodiment. It is nevertheless clear that the invention is susceptible to numerous variations which lie within the scope of its disclosure, in the framework of technical equivalents.

The invention claimed is:

1. A locking system to be fitted on a joint device equipped with means of control of the relative range of motion (R.O.M.) between two rods or uprights connected to it, said joint device comprising a pair of plates connected to each other by means of rivets and to said rods or uprights protruding from the joint device, wherein said system comprises at least one locking device comprising a stop member which is inserted between respective rods and plates connected to a fixed central element of the joint device, said stop member being activated to move from a retracted position to an inserted position in the joint device, at right angles in respect of the plane of the plate, by means of a cursor element sliding on a slide positioned in the upper part of a bridge element, said cursor element comprising a sloping surface which causes the movement of the stop member from a retracted to an inserted position.

2. The locking system of claim 1, wherein the insertion of the stop member, which takes place through a slot in the plate, prevents the relative movement of the plate and the rod of the joint device.

3. The locking system of claim 1, wherein the insertion of the stop member is achieved thanks to said sloping surface present on the lower edge of said cursor element which, by sliding in the slide positioned in the upper part of said bridge element fixed on a plate, pushes said stop member inside the joint device, sliding on the crest of said sloping surface.

4. The locking system of claim 1, wherein the two ends of the sloping surface of the cursor element include recesses which make it possible to determine a snap-locking during the movement of said cursor element.

5. The locking system of claim 1, wherein the sloping surface is inclined by a predetermined angle, thereby determining a given distribution in a vectorial way of the resulting force Ft when thrust is applied on said cursor element, whereby a vertical force component Fy acts along the axis of said stop member, so that the latter is inserted in a slot positioned in the central part of the plate in which the stop member slides.

6. The locking system of claim 1, further comprising a pair of springs that operate on respective parallel pins which are inserted in the stop member.

7. The locking system of claim 6, wherein the springs comprise holes to accommodate pins protruding from the bridge element and hold them in position.

8. The locking system of claim 1, wherein the upper end of said stop member comprises an enlarged portion which prevents the stop member from excessively penetrating the slot in the plate.

9. The locking system of claim 1, further comprising a cap with an opening for the sliding of a thrust element of the cursor element and a width which defines the maximum and minimum ("M") travel of the cursor element.

* * * * *